United States Patent [19]

Fleming

[11] Patent Number: 4,766,080
[45] Date of Patent: Aug. 23, 1988

[54] QUANTITATIVE MEASUREMENT OF LITHIUM

[75] Inventor: Roger Fleming, Niles, Mich.

[73] Assignee: Miles Inc., Elkhart, Ind.

[21] Appl. No.: 90,765

[22] Filed: Aug. 28, 1987

[51] Int. Cl.$^4$ ...................... G01N 33/00; G01N 21/00
[52] U.S. Cl. ........................................ 436/74; 436/79; 436/164; 436/909
[58] Field of Search ...................... 436/74, 79, 34, 164; 436/909; 422/73

[56] References Cited

U.S. PATENT DOCUMENTS

| | | | |
|---|---|---|---|
| 4,069,017 | 1/1978 | Wu et al. ............................... | 422/56 |
| 4,639,424 | 1/1987 | Wong .................................... | 436/79 |

OTHER PUBLICATIONS

Kapuscinski et al., Denaturnation of Nucleic Acids Introduced by Intercalating Agents Biochemical and Biophysical Properties of Acridine Orange-DNA Complexes, Journal of Biochemical Structure and Dynamics, vol. I, Issue No. VI, 1984.

Kojima et al., CA87(16):126584h.

Primary Examiner—Michael S. Marcus
Assistant Examiner—Lyle Alfandary-Alexander
Attorney, Agent, or Firm—Daniel W. Collins

[57] ABSTRACT

A method for the quantitative determination of lithium in a liquid test sample employing turbidimetric or nephelometric techniques to measure the maximum rate of change in the optical density of a reaction mixture containing precipitated lithium. The lithium is precipitated by a lithium precipitating reagent to result in dispersed, suspended particles, and the maximum rate of change in optical density determined to provide a linear dose response which can be quantitatively correlated to the amount of lithium present in the test sample.

10 Claims, 4 Drawing Sheets

QUANTITATIVE MEASUREMENT OF LITHIUM

BACKGROUND OF THE INVENTION

The present invention relates to the quantitative determination of the amount of lithium in a liquid test sample. In particular, the present invention is directed to nephelometric and turbidimetric methods for the quantitative measurement of lithium at endogeneous and therapeutic concentrations in biological fluids.

The use of lithium as a mode of treating individuals suffering from acute mania is well known and, accordingly, lithium therapy has become widely accepted as one of the major regimens for the treatment of this condition and for the prevention of relapse in recurrent bipolar mood disorders. In particular, depending upon the severity, the initial dosage of lithium is usually from between about 1,800–3,600 mg/day during acute stages of the condition and 600–1,200 mg/day for less severe, chronic conditions. From between about 1.0–1.6 mequiv./liter during acute therapy and 0.5–1.0 mequiv./liter during chronic therapy are generally considered optimal levels. However, since in some instances indications of toxicity have been observed with blood levels of 1.5 mequiv./liter, and blood levels of 5.0 mequiv./liter are generally considered potentially lethal, close monitoring of blood levels and dose adjustment until an adequate response is achieved is therefore required. Accordingly, there is a need for a convenient, quantitative and standardized clinical procedure, together with corresponding reference ranges, for detecting toxic concentrations of lithium.

Various techniques and methods for the quantitative determination or measurement of lithium in a liquid test medium are known, but, have been limited, for the most part, to flame absorption spectrophotometry and emission flame photometry [Rose, et. al, *Am. J. Clin. Pathol.*, Vol. 74, p. 521(1980)]. These methods require expensive and hazardous instruments and experienced technicians for their operation. Although other methods have been proposed which obviate the need for such instruments, including colorimetric and titrimetric methods, they nevertheless require complicated and often tedious, time consuming procedures to obtain quantitative measurements. Where less tedious or simpler methods have been proposed, quantitation has been sacrificed for semi-quantitative or qualitative results.

In particular, lithium assays and detection protocols have been described which involve a known reaction of iron ($Fe^{+3}$) and a salt radical of periodic acid ($IO_4^-$) with lithium to form a precipitate. The precipitate is then dissolved with a potassium hydroxide solution containing potassium iodate to form a pale yellow precipitate. However, when these reagents are employed in such assays, it is necessary to compare the reaction solution with a sodium chloride test solution when a considerable amount of sodium is present in the test sample. [Procke, et al., *Mikrochim. acta*, Vol. 3, p. 105 (1938)].

The gravimetric analysis of lithium in a prepared test solution where lithium is precipitated as a complex periodate by a strongly alkaline potassium periodate solution has also been described. The lithium periodate precipitate is then removed by filtration, dissolved in dilute sulfuric acid, and the periodate titrated with a standardized thiosulfate or arsenite solution. [Rogers, et al., *Ind. Eng. Chem.*, Anal. Ed., Vol. 15, p. 209 (1943)]. Although lithium can be distinguished from other alkali metals, all metals except those of the alkali group must first be removed according to such method, as well as ammonia when more than a few milligrams are present.

In a volumetric method for the determination of lithium, the quantitative precipitation of lithium fluoride in alcohol for the analysis of concentrated solutions of lithium chloride and lithium nitrate is described. [Baumann, *Analytical Chemistry*, Vol. 40, No. 11, p. 1731 (1968)]. However, this technique lacks sensitivity and selectivity over sodium and, moreover, since it is performed in an alcohol solution, it could not be used for analyzing serum samples without prior removal of endogenous protein.

A colorimetric method for the semi-quantitative determination of lithium in serum pretreated with trichloroacetic acid has also been described [Plum, *Clinica Chimica Acta*, Vol. 2, p. 67(1957)]. According to such method, the pretreated serum is combined with potassium hydroxide, sodium chloride, and a reagent comprising potassium metaperiodate, potassium hydroxide and ferric chloride. The resulting reaction solution containing a yellow lithium precipitate was then spectrophotometrically analyzed at 720 nm., and an attempt to construct a standard curve (optical density vs. time) employing an end-point analysis was made. However, such attempt was unsuccessful due to the presence of lipids in the test sample and, accordingly, such method does not provide an exact or quantitative determination of lithium.

In particular, such method involves tedious sample pretreatment steps which remove the endogenous turbidity associated with varying serum proteins, but which do not remove lipids. Since it has been shown that the presence of lipids contributes to the background optical density of a test sample, any variation in serum lipid content, even after removal of the serum proteins, could cause variability in the apparent lithium content according to such method. Furthermore, since it is known that the time of the maximum optical density change per second decreases as the lithium concentration increases, a sample blank from the optical density values would still be unsuccessful. Concomitantly, the absolute optical density of a sample of high lithium content is proportionately higher than that of a sample of low lithium content for early read times and proportionately lower than a sample of low lithium content for later read times. Therefore, taking an optical density measurement at a fixed time would yield a nonlinear standard curve, the shape of which would be determined by the exact read time. While lack of linearity does not preclude quantitation, the optical density of the sample blank does not change with time. Subtraction of a sample blank would therefore have different effects on samples of different lithium content. Therefore lipids would nevertheless still interfere with the lithium determination with sample blanking. In particular, quantitation cannot be achieved by reading optical density at a fixed read time with or without sample blanking, because if the sample incubation is permitted to continue for periods of time even greater than 300 seconds, the particles responsible for the turbidity aggregate and drop out of solution to cause considerable and untolerable variability.

A method employing similar reagents has also been described, but also provides only qualitative results. [Feigl, *Spot Tests In Inorganic Analysis*, Elsevier Publishing Co., New York, N.Y., 5th ed., p. 233 (1958)].

Accordingly, it is an object of the present invention to provide a quantitative method for the detection of therapeutic concentrations of lithium in a liquid test sample, particularly biological test samples.

Another object of the present invention is to provide a quantitative method for the detection of lithium in a liquid test sample employing instruments which are safe, convenient, and easily operated.

Further, it is an object of the present invention to provide a quantitative method for the detection of lithium in a liquid test sample which does not require the removal or minimization of lipids or proteins present in a serum sample.

SUMMARY OF THE INVENTION

It has now been observed that employing reagents as heretofore described but conducting the data analysis by determination of the maximum rate of optical density change per second, rather than measurement of optical density as an endpoint, not only permits quantitation of lithium independent from interfering background turbidity, but also precludes the need for tedious and time consuming sample pretreatment.

In an attempt to provide a quantitative method for the detection of lithium in a liquid test sample by endpoint colorimetry, the optical density of a test sample containing lithium and a lithium precipitating reagent, and an aqueous test sample (blank) containing lithium without the lithium precipitating reagent, were measured at a fixed end-point in time. Although it was expected that the use of blank would reduce the variability of the measurement of the test sample containing the lithium precipitating reagent as a result of the endogeneous turbidity thereof, such analysis was unsuccessful since the kinetics of turbidity development were found to be dependent upon the concentration of lithium. Accordingly, since the turbidity of a test sample containing lithium increases greater than proportionately as the concentration of lithium increases, a linear standard curve cannot be developed from which lithium can be quantitated. Furthermore, a poor dose response was observed for test samples containing from between 0 and 1.0mM lithium, which is an important clinical range for the determination of lithium in a liquid test sample from a patient being treated with lithium as described above.

It has now been found that lithium can be quantitatively determined by measuring the maximum rate of change in optical density over a period of time of a test sample containing lithium which is reacted with a lithium precipitating reagent. According to the method, a reaction mixture is formed comprising a liquid test sample containing lithium and a lithium precipitating reagent whereby substantially all of the lithium present in the reaction mixture is precipitated as lithium periodates in the form of dispersed, suspended particles. The maximum rate of change in optical density of the reaction mixture is then determined by directing a beam of light into the reaction mixture and measuring either the intensity of light transmitted through the reaction mixture (turbidimetric analysis) or scattered by the dispersed, suspended particles (nephelometric analysis) over a period of time. The maximum rate of change in the intensity of light transmitted or scattered during such period of time results in a linear dose response which can be employed to construct a standard curve and the amount of lithium present in the liquid test sample determined therefrom.

According to the present invention, the optical density of the reaction mixture can be measured at substantially any wavelength which is not interfered with by other species in the reaction mixture which would absorb light at the chosen wavelength. Furthermore, pretreatment of a test sample to remove the endogenous turbidity thereof caused by, for example, the presence of proteins, triglycerides, cholesterol, and the like, is not required by the present invention since the optical density of the reaction mixture caused by such turbidity is measured and accounted for upon commencement of the measurement of the rate of change in turbidity caused by the precipitated lithium.

DESCRIPTION OF THE PREFERRED EMBODIMENTS

Figure 1:
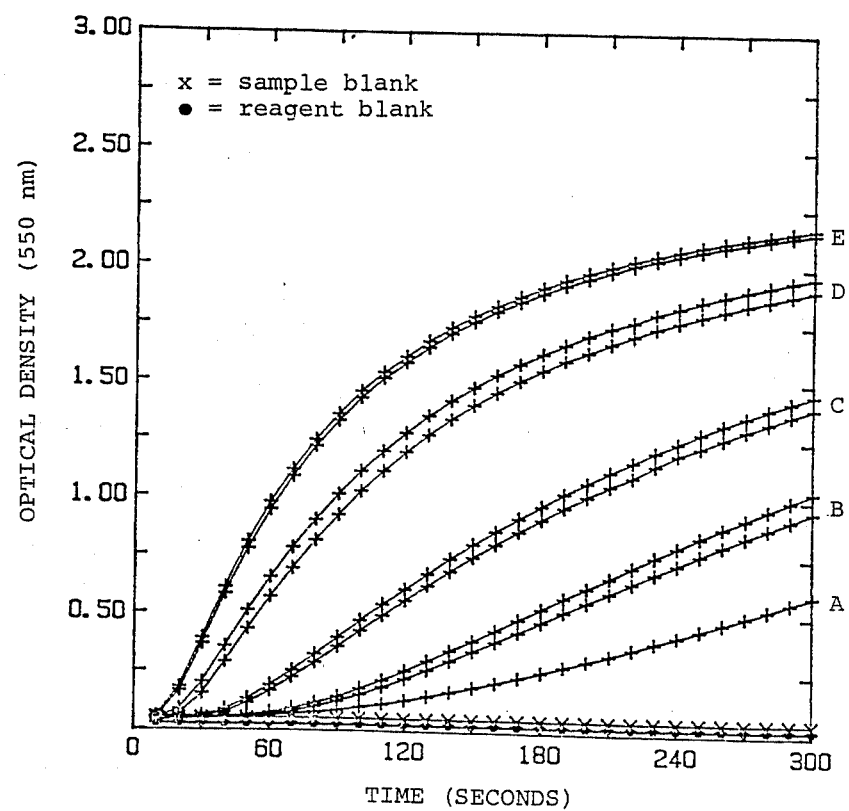
FIG. 1 is a graph which illustrates the change of optical density of lithium test samples containing a predetermined concentration level (low) of lipids.

According to the present invention, the determination of the amount of lithium present in a liquid test sample is based upon the maximum rate of change in the optical density or turbidity, of the reaction mixture caused by the precipitation of any lithium present by the lithium precipitating reagent. Although the optical density of an endogeneously turbid reaction mixture caused by the presence of potential interferants such as proteins, triglycerides, cholesterol, and the like, is accounted for upon commencement of the measurement of the rate of change in turbidity as described above, according to the present invention, such endogeneous turbidity will not substantially interfere with the measurement of the rate of change in turbidity caused by the precipitated lithium. However, it is to be understood that the precipitation of such potential interferants by the lithium precipitating reagent during such measurement would nevertheless contribute to the turbidity of the reaction mixture and would therefore interfere with the measurement of the rate of change in turbidity caused by the precipitated lithium. Accordingly, the lithium precipitating reagent is one which is capable of precipitating any lithium present in the reaction mixture without precipitating such potential interferants.

Lithium Precipitating Reagent

The lithium precipitating reagent is an alkaline transition metal periodate reagent which is formed in situ and which reacts with lithium to form an insoluble complex thereof comprising lithium periodates. In particular, the alkaline transition metal periodate reagent comprises a transition metal periodate compound which is formed in situ by combining a periodate reagent, such as potassium metaperiodate, sodium metaperiodate, sodium or potassium paraperiodate, or any other reagent which results in the in situ formulation of ferric periodate, with a transition metal salt reagent, such as ferric chloride, ruthenium chloride, osmium chloride, and the like. The periodate reagent is present in an amount from between about 0.5% and 8.0% (weight/volume), preferably 2.0%, and the transition metal salt is present in an amount from between about 0.1% and 1.0% (weight/volume), preferably 0.3%. The periodate reagent and the transition metal salt are combined with sodium chloride in an alkaline reaction solution, such as potassium hydroxide, sodium hydroxide, and the like. The alkaline reaction solution is from between about 0.1N and 1.5N, preferably 1.14N. The reaction of the aforementioned reagents results in the formation of iron periodate, ruthenium periodate, osmium periodate, and the like metal periodates, respectively. Preferably, the lithium precipitating reagent is alkaline iron periodate formed in situ by combining 2.0% (weight/volume) potassium metaperiodate and 0.3% (weight/volume) ferric chloride in a 1.14N potassium hydroxide solution.

It is to be understood that the alkaline reaction solution is of a sufficient concentration to maintain the pH of the periodate reagent/metal salt solution from between about pH 12.0 and pH 14.0, preferably pH 13.8.

Method

According to the method of the present invention, a liquid reaction mixture is formed comprising a liquid test sample suspected to contain lithium and the lithium precipitating reagent as described above, and a concentrated salt solution, such as sodium chloride. The liquid test sample containing lithium can be a naturally occurring or artificially formed liquid suspected to contain lithium, and is usually a biological fluid or a dilution thereof. Such biological fluids include serum, whole blood, plasma, urine, saliva, and amniotic and cerebrospinal fluids.

As described above, the method of the present invention does not require pretreatment of the test sample to remove any species of potential interferants which may be present and contribute to the inherent turbidity of the test sample. However, it is to be understood that if desired, and although not required, the test sample can nevertheless be treated with reagents to remove such potential interferants or otherwise decrease or eliminate the endogenous turbidity resulting therefrom. Such reagents include, but are not intended to be limited to, trichloroacetic acid for proteins; chloroform, methylene chloride and toluene for cholesterol and triglycerides; and 8-hydroxyquinoline, phenanthroline, and ion exchange resins, for biological metals.

In carrying out the method of the present invention, the liquid test sample, the lithium precipitating reagent, and the concentrated salt solution, are heated to, and the liquid reaction mixture maintained at, from between about 35° C. and 48° C., preferably 37° C. The concentrated salt solution can generally be from between about a 2.0N and a saturated solution thereof, preferablay 4.5N. Any lithium present in the reaction mixture reacts with the lithium precipitating reagent to result in lithium periodate complexes in the form of dispersed, suspended particles thereof. The formation of such dispersed, suspended lithium periodate complex particles result in a change in the optical density of the reaction mixture whereby the maximum rate of change in such optical density over a period of time is determined.

The maximum rate of change in the optical density of the reaction mixture is determined employing a spectrophotometer, such as an OPTIMATE ® liquid analyzer (Miles Laboratories, Inc., Elkhart, Ind., USA) or other such instrument known in the art, which is capable of measuring the intensity of light transmitted through a liquid medium (i.e., turbidimetric) or scattered by a liquid medium (i.e., nephelometric). In particular, the liquid reaction mixture, or an aliquot thereof, is deposited into a container adapted for use with such instrument, such as a cuvette, and a beam of light generated by the instrument directed therethrough. Where the intensity of light transmitted through the reaction mixture is measured, a sensing mechanism, positioned approximately 180° relative to the light source, receives and measures the intensity of the light beam which is transmitted through the reaction mixture, i.e., not absorbed by the dispersed, suspended lithium periodate complex particles contained therein. Where the intensity of light scattered by the dispersed, suspended lithium periodate complex particles is measured, a sensing mechanism, positioned from between about 1° and 179°, preferably 90°, relative to the light source, receives and measures the intensity of light scattered by the lithium periodate complex particles.

It is to be understood that the wavelength of the light beam generated by the particular instrument being employed as described above can be any wavelength which is not absorbed by any interfering species which might be present in the liquid reaction mixture, and which can therefore be determined by one skilled in the art. For example, where red blood cells are present in the liquid reaction mixture, a wavelength is chosen which would not be absorbed by the red blood cells, i.e., a wavelength which is greater than about 640 nm. In addition to considering the presence of such interfering species when selecting a desired wavelength, the choice of wavelength also depends upon the desired sensitivity and the operating specifications of the particular instrument being employed. Preferably, the wavelength of the beam of light is from between about 350 nm and 900 nm, more preferably 550 nm.

The measurement of the intensity of light transmitted through or scattered by the reaction mixture as described above is made substantially immediately after the formation thereof. In particular, the optical density of the reaction mixture is first measured from between about 1 and 15 seconds after the reaction mixture is formed, preferably 10 seconds thereafter, and measured at from between about 5 and 15 second periodic intervals of time thereafter, preferably at 10 second periodic intervals of time thereafter. The measurements of the optical density of the reaction mixture at the aforementioned periodic intervals of time are made for from between about 10 seconds and 300 seconds.

Once the optical density of the reaction mixture has been measured at the periodic intervals described above over the 300 second time period, the rate of optical density change per second is calculated for at least three consecutive optical density measurements, starting at the initial optical density measurement. The rate of optical density change per second is then calculated for the 3 consecutive optical density measurements starting with the second optical density measurement through the fourth optical density measurement. The process of dropping one optical density measurement from the beginning of the measurement window and adding one at the end continues until the maximum optical density measurement per second is determined for a particular sample. Preterably, the optical density is measured at 10 second periodic intervals over a total of 300 seconds and the maximum rate is determined for 4 consecutive measurements.

Once the maximum optical density change per second is determined as described above, the values obtained therefrom result in a linear dose response, i.e., maximum rate of change of optical density (ordinate) vs. lithium concentration (abscissa), whereby as the concentration of lithium increases, the maximum rate of change of optical density increases. Accordingly, once such measurements have been made, and the maximum rate of change per second of optical density determined, the linear dose response obtained therefrom permits construction of a standard curve from which the amount of lithium present in the liquid test sample can be quantitatively determined.

In particular, the present invention will now be illustrated, but is not intended to be limited, by the following examples:

EXAMPLE 1

Lithium Precipitating Reagent

A lithium precipitating reagent solution comprising an alkaline iron periodate reagent which is capable of reacting with lithium to form dispersed, suspended lithium complex particles in a reaction mixture was prepared as follows:

Two (2.0) grams of potassium metaperiodate Mallinkrodt, Inc., St. Louis, Mo., USA) was dissolved in 10.0 ml of a 2.0N solution of potassium hydroxide, and diluted to a final volume of 50.0 ml with distilled water (twice distilled). Three (3.0) ml of a 10% (weight/volume) solution of ferric chloride was added to the 50 ml potassium metaperiodate solution and diluted to a final volume of 100 ml with 2.0N potassium hydroxide. The final concentrations of potassium metaperiodate, ferric chloride and potassium hydroxide in the reagent solution were 2.0% (weight/volume), 0.3% (weight/volume) and 1.14N, respectively.

EXAMPLE 2

Liquid Test Samples

A pool of normal human serum was prepared from clinical specimens (South Bend Medical Foundation, South Bend, Ind., USA) and analyzed on a SERALYZER ® reflectance photometer (Miles Diagnostics, Miles Laboratories, Inc., Elkhart, Ind., USA) for cholesterol and triglyceride levels. The serum pool was divided into three aliquots of 5.0 ml each, and the first aliquot identified as the normal pool containing the lowest levels of triglycerides and cholesterol, and the second and third aliquots were mixed with serum samples containing increased amounts of triglycerides and cholesterol. Each of the three 5.0 ml aliquots was further divided into five 1.0 ml aliquots and mixed with increasing volumes of 25mM lithium chloride and distilled water was added to each test sample to maintain a constant dilution effect. The concentration of lithium chloride in each aliquot was determined by flame atomic emission spectroscopy employing a IL943 Flame Photometer (Instrumentation Laboratory, Lexington, Mass., USA). The final concentrations of lithium, triglycerides and cholesterol in the liquid test samples are shown in Table 1.

TABLE 1

| Sample | Sample mL | 25 mM LiCl uL | Water ($\mu$L) | Lithium meq/L | Triglycerides mg/dL | Cholesterol mg/dL |
| --- | --- | --- | --- | --- | --- | --- |
| A | 1.00 | 0 | 154 | 0.00 | 115 | 183 |
| B | 1.00 | 26 | 128 | 0.57 | 115 | 183 |
| C | 1.00 | 53 | 101 | 1.15 | 115 | 183 |
| D | 1.00 | 107 | 47 | 2.30 | 115 | 183 |
| E | 1.00 | 154 | 0 | 3.29 | 115 | 183 |
| F | 1.00 | 0 | 154 | 0.00 | 211 | 201 |
| G | 1.00 | 26 | 128 | 0.57 | 211 | 201 |
| H | 1.00 | 53 | 101 | 1.15 | 211 | 201 |
| I | 1.00 | 107 | 47 | 2.33 | 211 | 201 |
| J | 1.00 | 154 | 0 | 3.33 | 211 | 201 |
| K | 1.00 | 0 | 154 | 0.00 | 370 | 290 |
| L | 1.00 | 26 | 128 | 0.56 | 370 | 290 |
| M | 1.00 | 53 | 101 | 1.16 | 370 | 290 |
| N | 1.00 | 107 | 47 | 2.31 | 370 | 290 |
| O | 1.00 | 154 | 0 | 3.32 | 370 | 290 |

EXAMPLE 3

Turbidimetric Measurement of Lithium

The amount of lithium in each of the liquid test samples prepared according to Example 2 was determined according to the method of the present invention employing the lithium precipitating reagent prepared according to Example 1, as follows:

(i) Each of the liquid test samples, the lithium precipitating reagent, and a 4.5N aqueous sodium chloride solution were, independently, heated to and maintained at 37° C.

(ii) Reaction mixtures were formed, independently, comprising 200 $\mu$L of a liquid test sample, 400 $\mu$L of the lithium precipitating reagent and 200 $\mu$L of the 4.5N sodium chloride solution, to result in a final concentration of 1.0% (weight/volume) potassium metaperiodate, 0.15% (weight/volume) ferric chloride, 0.57N potassium hydroxide, 1.125N sodium chloride, and 25% (volume/volume) serum.

(iii) The reaction mixtures from step (ii) were, independently, immediately aspirated into a heated (37° C.) flow cell of a Beckman DU-8 ® Spectrophotometer (Beckmann Instruments, Fullerton, Calif., USA), and the optical density thereof measured at 550 nm at periodic intervals of 10 seconds for a 300 second period of time. The flow cell was rinsed with 100mM HCl, followed by distilled water, after the measurement of the optical density of each reaction mixture was made.

Analysis

Figure 2:
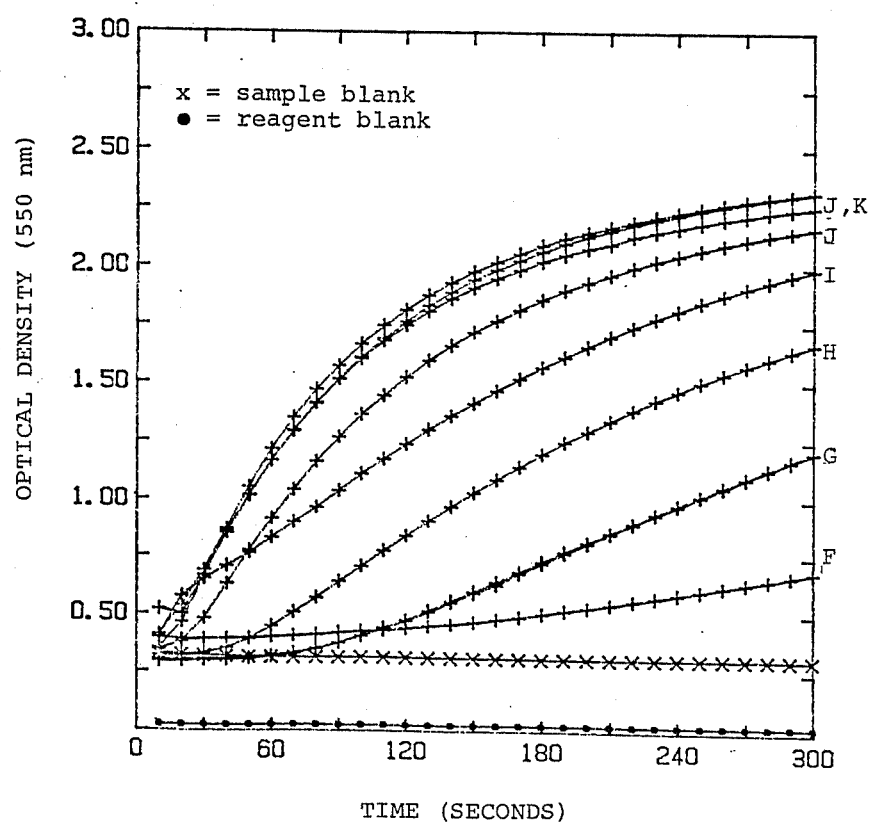
FIG. 2 is a graph which illustrates the change of optical density of lithium test samples containing a predetermined concentration level (medium) of lipids.
Figure 3:
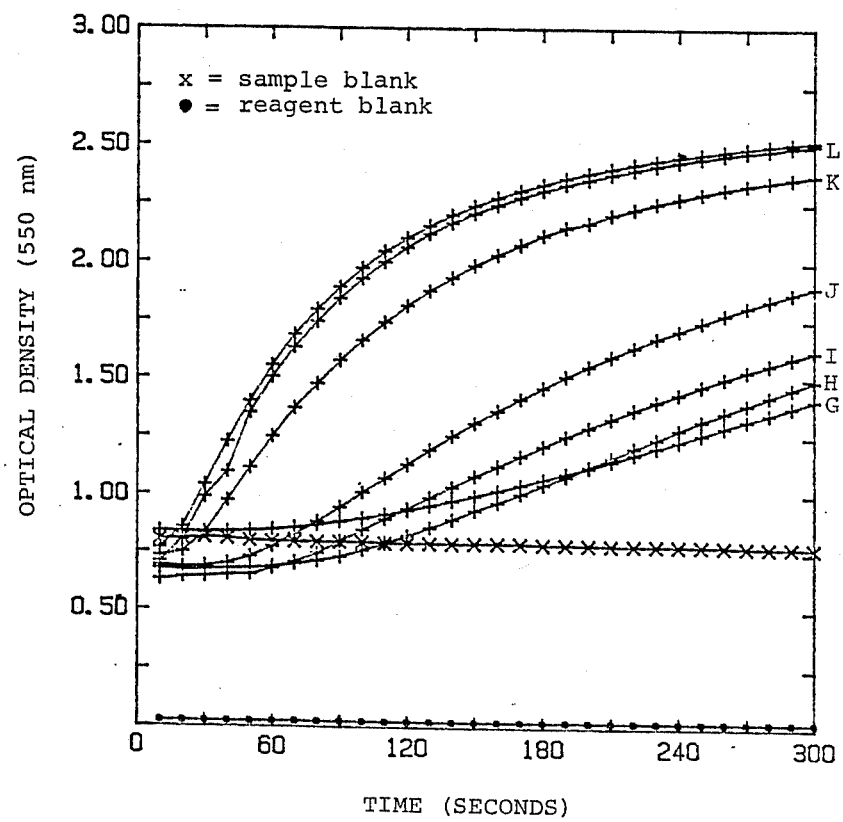
FIG. 3 is a graph which illustrates the change of optical density of lithium test sample containing a predetermined concentration level (high) of lipids.

Kinetic profiles (FIGS. 1–3) were analyzed to determine the four consecutive absorbance points which yielded the maximum absorbance change with time (optical density/second). The maximum optical density/second was used as the sample reactivity in determining lithium response. A reagent blank was assayed (substituting water for sample) and no increase from an optical density of 0.043 was observed over the 300 second period of measurement. Sample blanks (substitution of water for the reagent) exhibited no significant kinetics but did exhibit an increase in background optical density as the triglyceride and cholesterol levels increased.

Figure 4:
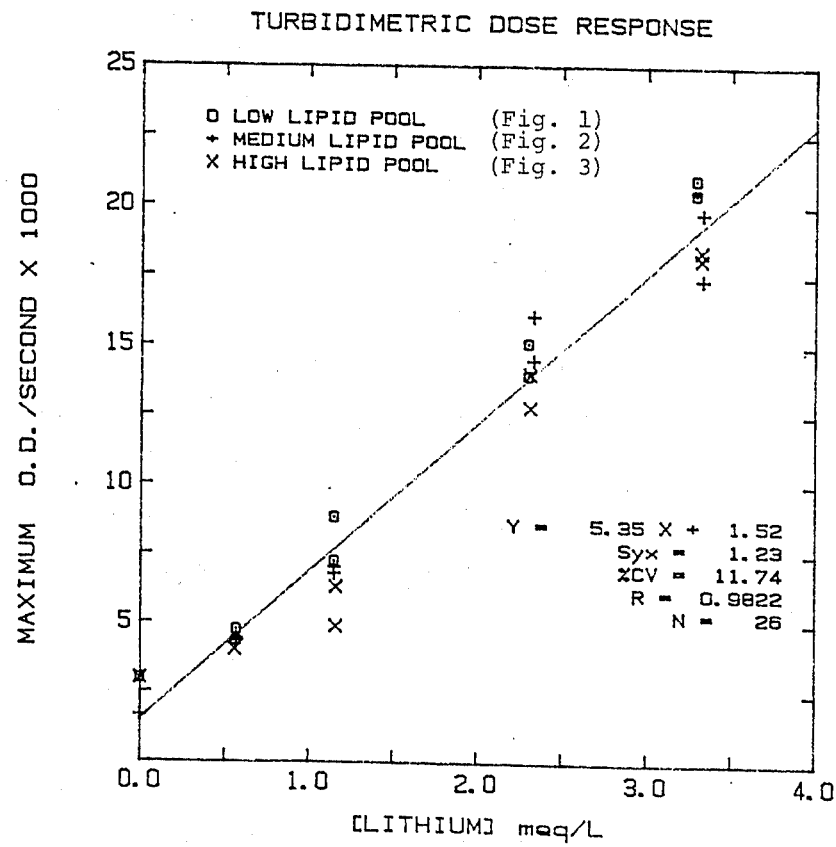
FIG. 4 is a graph which illustrates the linear dose response of the lithium test samples obtained from the maximum rate of change of optical density determined from FIGS. 1-3.

Although the presence of the triglycerides and cholesterol resulted in endogeneous turbidity of the reaction mixture, the maximum rate of change in optical density/second increased with increasing concentrations of lithium (Table 2, FIG. 4), rather than increasing as a function of lipid concentration. Furthermore, the insensitivity to sodium and potassium according to the method of the present invention is demonstrable by the lack of turbidity in the reagent blanks, and any variation in sample concentration of such electrolytes would be compensated for by the high reagent concentrations thereof.

TABLE 2

| Sample | Max Rate OD/Second × 1000 | Time of Max Rate (seconds) |
|---|---|---|
| A | 2.97 | 270–300 |
| B | 4.34 | 160–190 |
| B | 4.74 | 150–180 |
| C | 7.24 | 80–110 |
| C | 6.81 | 70–100 |
| D | 13.94 | 30–60 |
| D | 15.1 | 30–60 |
| E | 20.47 | 20–50 |
| E | 20.99 | 20–50 |
| F | 1.67 | 270–300 |
| G | 4.34 | 150–180 |
| G | 4.42 | 160–190 |
| H | 7.02 | 70–100 |
| H | 6.79 | 80–110 |
| I | 14.48 | 30–60 |
| I | 16.09 | 20–50 |
| J | 17.41 | 20–50 |
| J | 19.76 | 20–50 |
| K | 2.97 | 270–300 |
| L | 4.03 | 170–200 |
| M | 4.88 | 80–110 |
| M | 6.31 | 80–110 |
| N | 14.00 | 30–60 |
| N | 12.79 | 40–70 |
| O | 18.41 | 20–50 |
| O | 18.12 | 20–50 |

What is claimed is:

1. A method for quantitatively determining the amount of lithium in a liquid test sample, said method comprising the steps of:
   (a) forming a reaction mixture comprising said liquid test sample and a lithium precipitating reagent whereby substantially all of the lithium present therein is precipitated by said precipitating reagent in the form of dispersed, suspended particles in said reaction mixture;
   (b) directing a beam of light into said reaction mixture and measuring the intensity of light (i) transmitted through said reaction mixture, or (ii) scattered by said dispersed, suspended particles in said reaction mixture over a period of time; and
   (c) determining the rate of change in intensity of light transmitted or scattered, respectively, over said period of time whereby the rate of change in intensity thereof can be correlated to the amount of lithium in said liquid test sample.

2. The method of claim 1 wherein the rate of change in intensity of light transmitted through said reaction mixture is measured.

3. The method of claim 1 wherein the rate of change in intensity of light scattered by said dispersed, suspended particles is measured.

4. The method of claim 1 wherein said lithium precipitating reagent is an alkaline transition metal periodate reagent which reacts with lithium to form an insoluble complex comprising lithium periodates.

5. The method of claim 4 wherein said alkaline transition metal periodate reagent is formed in an alkaline reaction solution comprising a periodate reagent and a transition metal salt reagent.

6. The method of claim 5 wherein said alkaline transition metal periodate reagent is formed in a potassium hydroxide solution comprising potassium metaperiodate and ferric chloride.

7. The method of claim 1 wherein the pH of said reaction mixture is from between about pH 12.0 and pH 14.0.

8. The method of claim 1 wherein said liquid test sample is a biological fluid.

9. The method of claim 1 wherein the temperature of said reaction mixture is from between about 25° C. and 48° C.

10. The method of claim 1 wherein said liquid test sample is pretreated with trichloroacetic acid, chloroform, or 8-hydroxyquinoline.

* * * * *